US009724040B2

(12) United States Patent
Fort

(10) Patent No.: US 9,724,040 B2
(45) Date of Patent: Aug. 8, 2017

(54) GARMENT INTEGRATING A SYSTEM FOR COLLECTING PHYSIOLOGICAL DATA

(71) Applicant: Laurent Fort, Menton (FR)

(72) Inventor: Laurent Fort, Menton (FR)

( * ) Notice: Subject to any disclaimer, the term of this patent is extended or adjusted under 35 U.S.C. 154(b) by 0 days.

(21) Appl. No.: 14/434,714

(22) PCT Filed: Oct. 7, 2013

(86) PCT No.: PCT/EP2013/070791
§ 371 (c)(1),
(2) Date: Apr. 9, 2015

(87) PCT Pub. No.: WO2014/056827
PCT Pub. Date: Apr. 17, 2014

(65) Prior Publication Data
US 2015/0230752 A1    Aug. 20, 2015

(30) Foreign Application Priority Data
Oct. 9, 2012    (FR) ...................................... 12 59620

(51) Int. Cl.
*A61B 5/00*    (2006.01)
*A61B 5/0205*  (2006.01)
(Continued)

(52) U.S. Cl.
CPC .......... *A61B 5/6804* (2013.01); *A61B 5/0002* (2013.01); *A61B 5/0205* (2013.01);
(Continued)

(58) Field of Classification Search
USPC ................................................. 600/300–301
See application file for complete search history.

(56) References Cited

U.S. PATENT DOCUMENTS

| 4,633,881 A | 1/1987 | Moore et al. |
| 5,694,939 A | 12/1997 | Cowings |

(Continued)

FOREIGN PATENT DOCUMENTS

| AU | 2006/222732 B2 | 10/2006 |
| DE | 102 51 900 A1  | 5/2004 |

(Continued)

OTHER PUBLICATIONS

International Search Report dated Jan. 22, 2014, for International Application No. PCT/EP2013/070791; Applicant, Laurent Fort. (8 pages).

(Continued)

*Primary Examiner* — Nicole F Johnson
(74) *Attorney, Agent, or Firm* — McCracken & Gillen LLC

(57) ABSTRACT

The invention relates to a system for collecting physiological data comprising a data collection device comprising at least one sensor module so configured as to capture physiological measurements, and a monitoring system so configured as to retrieve and transmit the physiological measurements; the data collection device comprising a garment wherein the sensor module and the monitoring system are integrated, with the monitoring system comprising at least two housings connected together mechanically in a flexible manner so as to conform to the shape of a part of the body whereon the monitoring system is able to be positioned; at least one flexible connecting member for mechanically connecting the at least two housings; a data acquisition and wireless communication module positioned in one of the two housings; a motion detection module installed in one of the two housings.

19 Claims, 4 Drawing Sheets

(51) Int. Cl.
  *A61B 5/024* (2006.01)
  *A61B 5/08* (2006.01)
  *A61B 5/11* (2006.01)

(52) U.S. Cl.
  CPC ......... *A61B 5/02405* (2013.01); *A61B 5/0816* (2013.01); *A61B 5/1123* (2013.01)

(56) References Cited

U.S. PATENT DOCUMENTS

| | | | |
|---|---|---|---|
| 6,527,711 B1 * | 3/2003 | Stivoric | A61B 5/0002 128/898 |
| 2005/0143199 A1 | 6/2005 | Saroyan | |
| 2008/0027341 A1 | 1/2008 | Sackner et al. | |
| 2012/0176764 A1 | 7/2012 | Löher | |
| 2012/0246795 A1 | 10/2012 | Scheffler et al. | |

FOREIGN PATENT DOCUMENTS

| | | |
|---|---|---|
| DE | 10 2007/00232 A1 | 7/2008 |
| EP | 1 992 389 A1 | 11/2008 |
| FR | 2 917 298 A1 | 12/2008 |
| WO | WO 2008/029362 A2 | 3/2008 |
| WO | WO 2009/112494 A1 | 9/2009 |

OTHER PUBLICATIONS

Written Opinion dated Jan. 22, 2014, for International Application No. PCT/EP2013/070791; Applicant, Laurent Fort. (10 pages).

* cited by examiner

GARMENT INTEGRATING A SYSTEM FOR COLLECTING PHYSIOLOGICAL DATA

FIELD OF THE INVENTION

The present invention generally relates to a system for collecting physiological data and, in particular, to a system for advantageously collecting physiological measurements in real time integrated in a smart garment worn by a person such as a player or any other sports person.

STATE OF THE ART

Several devices are currently available for capturing and monitoring players' vital parameters, such as the heart rate or the respiratory rate or other physiological measurements. The players' parameters are recorded and analyzed in real time for medical and scientific purposes.

However, the existing monitoring equipment is not adapted to the possibility of being used for competition, because of its size and weight. In addition, some elements/modules of one piece of the monitoring equipment do not sufficiently comply with the shape of a player's body in that they may cross and thus collide.

Such disadvantages may cause the wearer of such equipment to be harmed during a training session or a game or simply demonstrate that the equipment is incompatible with the freedom of movement required by the sport in question.

A German patent application publication DE10251900 A1 discloses monitoring equipment comprising modules respectively so configured as to capture and retrieve physiological measurements and to remotely transmit data relating to the physiological measurements. Such equipment further comprises wires used for connecting the modules.

The modules of such monitoring equipment are not suitable for being placed on a body part having a curved surface such as a part of the wearer's collar. In addition, the modules may cross, which could result in the wearer being harmed, more particularly during a competition and/or in the retrieval of physiological measurements and/or the remote transmission of data relating to the physiological measurements being affected.

For the reasons of safety and convenience mentioned above, the invention aims at providing a system wherein the equipment worn by the player is optimized so as to reduce the size and the power consumption, and in particular to be able to better cooperate with a part of the equipment carrier's body whereon the equipment is capable of being placed.

The object of the present invention is to provide a solution that remedies at least some of such constraints. Other objects, characteristics and advantages of the present invention will become apparent upon reading the following description and referring to the appended drawings. It should be understood that other advantages can be incorporated.

SUMMARY OF THE INVENTION

The present invention makes it possible to overcome all or part of the drawbacks of the currently known techniques.

More particularly, one aspect of the invention relates to a system for collecting physiological data comprising a data collection device which comprises a garment, at least one sensor module integrated in the garment and so configured as to capture physiological measurements, and a monitoring system integrated in the garment and so configured as to retrieve and transmit information from the monitoring system and in particular the physiological measurements and/or the motion data, preferentially in real time.

The monitoring system, in a preferred case, comprises at least: two housings connected together mechanically, advantageously in a flexible manner, to conform to the shape of a part of the body, if possible, in a little dangerous place, whereon the monitoring system is adapted to be placed; at least one flexible connecting member for mechanically connecting the at least two housings; a data acquisition and wireless communication module installed in one of the at least two housings and so configured as to retrieve the physiological measurements, and a motion detection module installed in one of the two cases, electrically connected to the data acquisition and wireless communication module and so configured as to capture motion data, the data acquisition and wireless communication module being so configured as to retrieve and send the physiological measurements and the motion data to a remote receiver.

In addition, the system for collecting physiological data may also comprise a communication system comprising a plurality of transmission relays so configured as to route the data, and a server so configured as to receive the plurality of transmission relays and store the physiological measurements.

The invention thus provides a system making it possible to capture, and transmit a player's physiological measurements so as to analyze and monitor the health and energy expenditure of the garment wearer, specifically his/her cardiopulmonary mechanisms during training sessions or games. Thanks to the soft/flexible material it is made of, the data collection equipment carried by the player can comply with the shape of a part of the body of the equipment carrier whereon the equipment is adapted to be placed, which is one of the possible advantages of the invention.

BRIEF DESCRIPTION OF THE FIGURES

The aims, objects, characteristics and advantages of the invention will better emerge from the detailed description of one embodiment thereof which is illustrated by the following appended drawings wherein.

Figure 1:
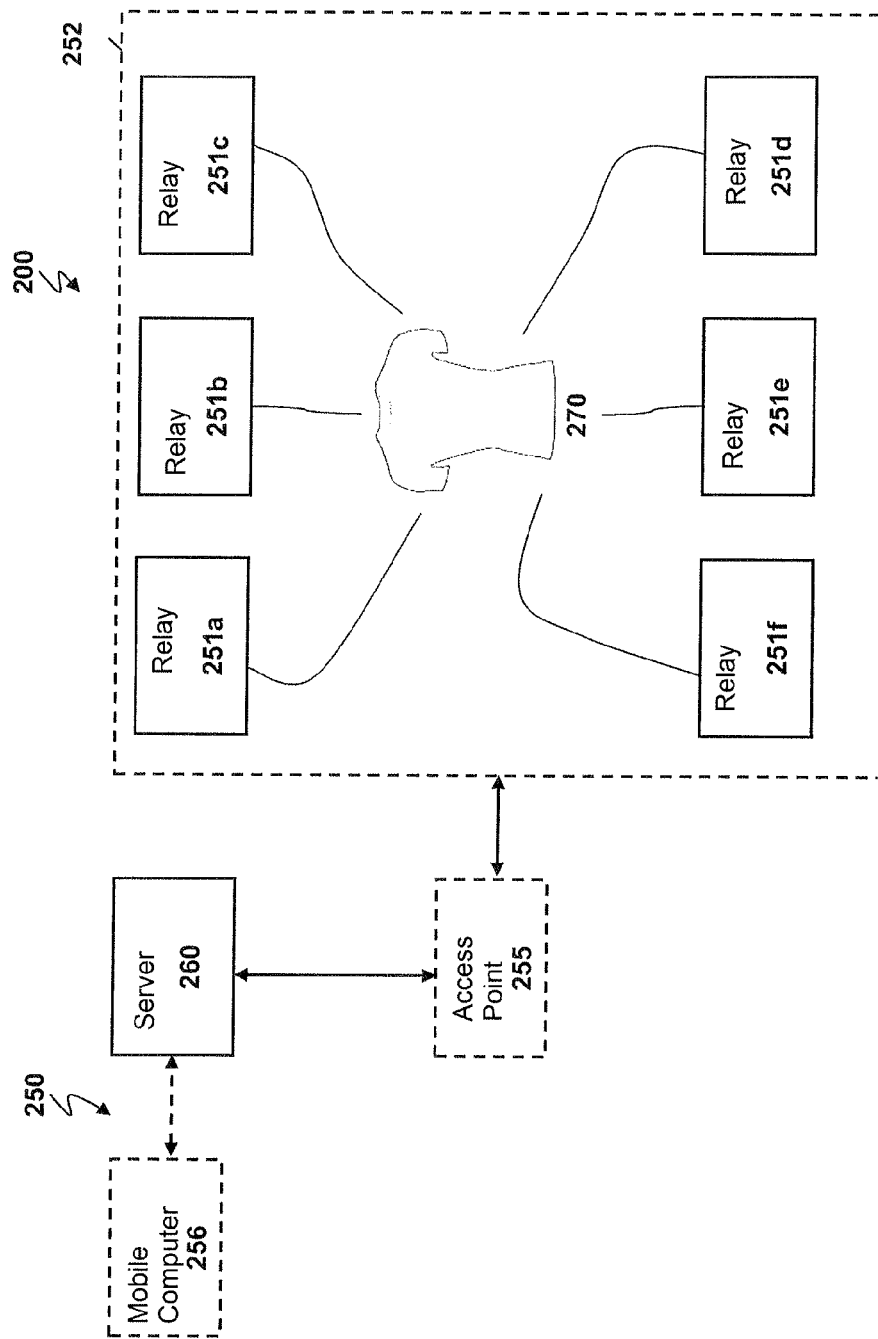
FIG. 1 shows the overall structure of a system for collecting physiological data according to one embodiment of the present invention.

The drawings are given as examples and are not restrictive to the invention. They are schematic representations in principle intended to facilitate the understanding of the invention and are not necessarily to scale with practical applications. In particular, the relative sizes of the various elements illustrated in the Figures are not representative of reality.

DETAILED DESCRIPTION OF THE INVENTION

Prior to beginning a detailed review of the various embodiments of the invention, optional characteristics are mentioned hereunder, which can potentially be used in combination or alternately:

the at least one connection member is deformable in bend in one direction and rigid in the other directions.

the at least one connecting member is in the form of a strap.

the at least one connecting member is made of a polymeric material.

the at least one connecting member is so configured as to electrically connect the at least two housings.

the data acquisition and wireless communication module is installed in a first housing, the motion detection module is installed in a second housing; the monitoring system comprises:

a power source module installed in a third housing and electrically connected to the data acquisition and wireless communication module and to the motion detection module, respectively, a first connecting member so configured as to mechanically connect the first and third housings, and a second connecting member so configured as to mechanically connect the second and third housings.

at least one housing comprises a coating made of elastomeric material.

at least one housing of the monitoring system comprises at least one snap button connected to the sensor module via at least one wire of a wired electrical connection system, and so configured as to fasten the at least one housing to the garment.

the at least one wire of the wired electrical connection system is inserted into a wire passage between the back and the front of the garment (the channel being formed for example with at least one seam).

the monitoring system is integrated at a collar part of the garment.

the sensor module comprises at least a textile electrode and/or one textile membrane so configured as to capture the physiological measurements such as cardiac data and a respiration rate, the data acquisition and wireless communication module is a radio module.

the system for collecting physiological data comprises a communication system comprising a plurality of transmission relays so configured as to route the physiological measurements and/or the motion data, and a server so configured as to receive from the plurality of transmission relays and to store the physiological measurements and/or the motion data.

the plurality of transmission relays is installed so as to surround a zone of displacement.

the position of the monitoring system is detected by triangulation from at least three of said transmission relays, a communication between the plurality of transmission relays and the data acquisition and wireless communication module complies with a radio communication protocol, the frequency of which is below 928 MHz, and the power of which is below 10 dBm.

the plurality of transmission relays and the server communicate through a communication network comprising at least a portion of wireless communication from the plurality of transmission relays, the frequency and the power of the portion of wireless communication are above those allowed by the radio communication protocol, the communication system comprises an access point so configured as to transmit to the server the physiological measurements and/or the motion data sent from the plurality of transmission relays, with the access point being either connected to the server by an Internet connection or installed in a device comprising the server.

FIG. 1 shows the overall structure of the system for collecting physiological data 200 according to one embodiment of the present invention. The system for collecting physiological data 200 comprises a data collection equipment 270 carried by a player and so configured as to collect the player's physiological measurements during a game, and a communication system 250 so configured as to transmit and store the physiological measurements.

The system also advantageously enables the measurement, the acquisition and the transmission of motion data. Motion data means any information about the situation of the wearer in space and any evolution (displacement) of such situation. This may particularly include: an inclination (rotation) along one or more axes, a translation along one or more axes, a travelling speed during at least one rotation and/or at least one translation, or still at least acceleration during the above movements. Such data may also include interpretive data of the information on the above motions; it includes, in particular, information on the energy expenditure or the power produced, during an effort, for example.

The data collection device 270 comprises a sensor module 210, a monitoring system 220 and a garment 205. In such embodiment, the garment 205 is a T-shirt worn by the player during the game. The example given in the detailed description is that of a person carrying the equipment who is a player in a sport, especially football. However, such case is in no way restrictive, and the invention can be used by any other wearer who would like to use it.

Figure 2:
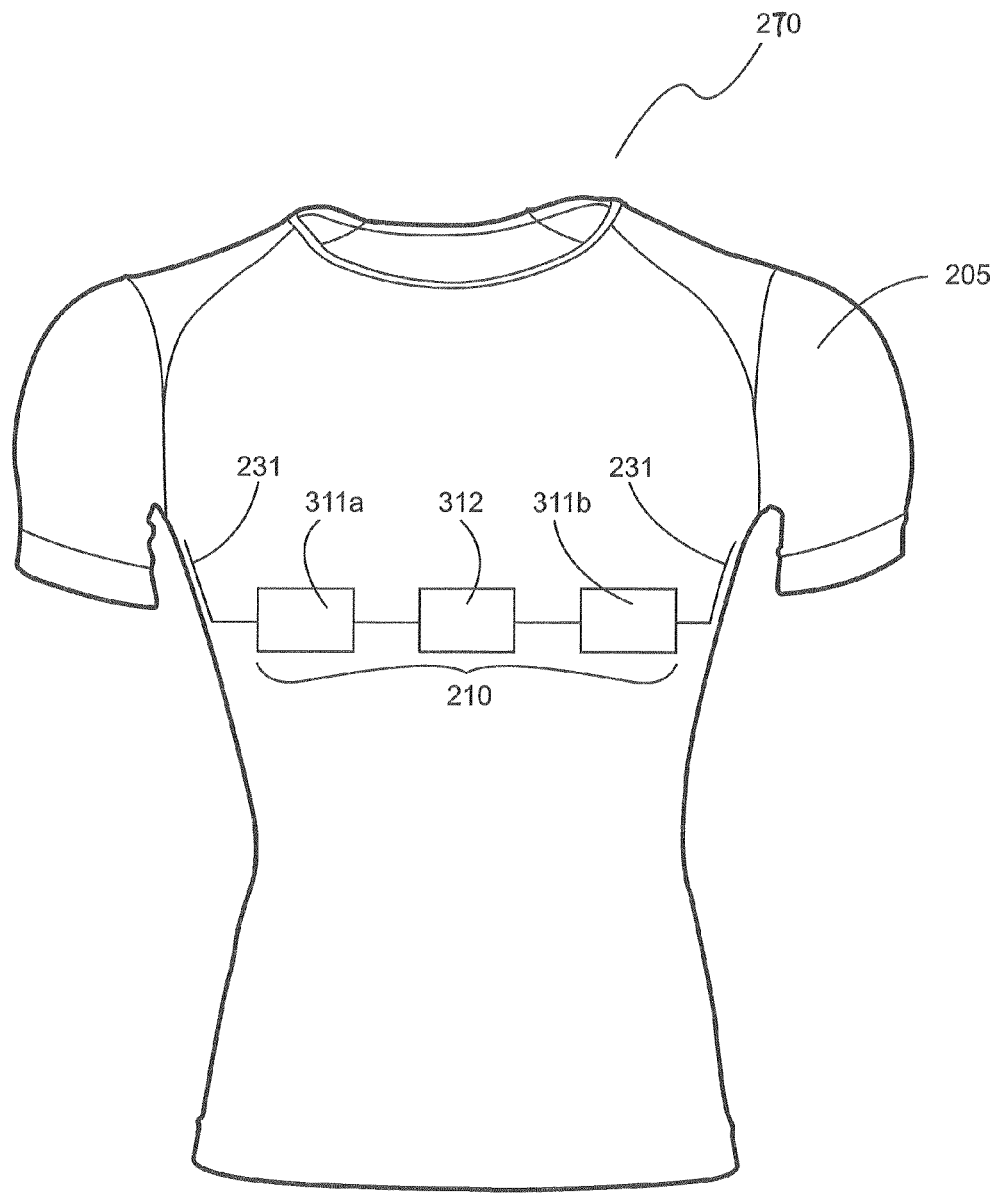
FIG. 2 shows a capture module integrated in the front side of a T-shirt according to the embodiment of the present invention.

The sensor module 210 is integrated in the front side of the T-shirt 205 as shown in FIG. 2, and is so configured as to capture the player's physiological measurements. It is advantageously located in a torso portion of the garment 205. In the embodiment shown, the sensor module 210 comprises two textile electrodes 311a, 311b and one textile membrane 312 installed in the chest portion of the T-Shirt 205 and so configured as to capture several types of physiological measurements. The textile electrodes 311a, 311b are so configured as to measure the heart rate, the variability of the heart rate, etc. The textile membrane 312 is so installed as to measure the respiration rate, etc. In one preferred embodiment, the sensor module 210 also comprises a strain gauge placed on the chest portion of the T-Shirt 205 in order to measure the variation in volume of the thorax of the person wearing the T-shirt 205.

The module sensor 210 is connected to the monitoring system 220 via a wire 231 of a wired electrical connection system 230. Preferably, but not restrictively, the wire 231 of the wired electrical connection system 230 is inserted into a wire passage (not shown in the Figures) between the back and the front of the T-shirt 205.

The sensor module 210 of the invention is not limited to the textile electrodes and membranes mentioned above. Other devices for measuring other types of physiological measurements such as the number of steps or the energy expenditure (MET) can be performed without departing from the scope of the present invention. Besides, the invention may be used to acquire other data than those related to the wearer's physiology. As will be seen later, the invention can also provide a location indication. Other sensors may also be implemented.

Figure 3A:
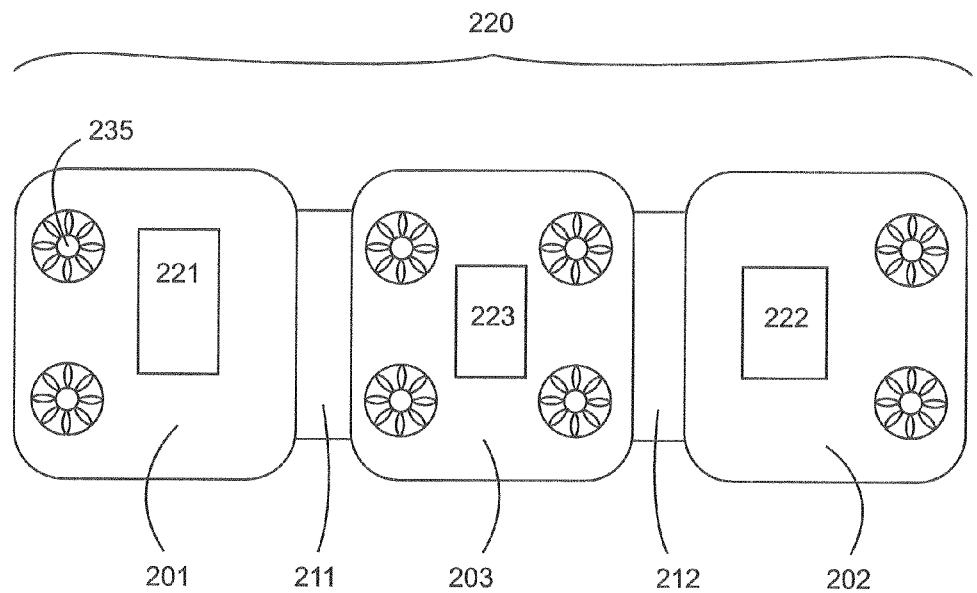
FIG. 3a shows the structure of a monitoring system according to the embodiment of the invention.
Figure 3B:
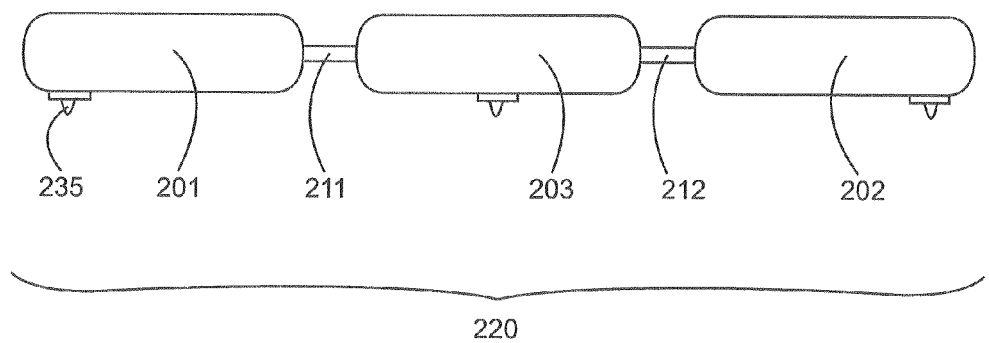
FIG. 3b shows the cross section of the monitoring system according to the embodiment of the invention.

FIG. 3a shows the structure of the monitoring system 220 according to one embodiment of the invention. FIG. 3b shows the cross section of the monitoring system 220 according to such embodiment of the invention. The monitoring system 220 is so configured as to retrieve the physiological measurements captured and sent from the sensor module 210, and to send these to the server 260 via the communication system 250. The monitoring system 220 in such case comprises: a data acquisition and wireless communication module 222, a motion detecting module 221, preferably but not restrictively as regards its location, a power source module 223, three housings 201, 202, 203, two connecting members 211, 212 and snap buttons 235.

The motion detection module 221 advantageously comprises at least one motion sensor. The current techniques provide sensors with reduced sizes and reduced consumption that will give satisfaction. In particular, MEMS (Micro-Electro-Mechanical Systems) sensors can be used. They may be accelerometers having one or more axes or gyroscopes having one or more axes. Such sensor(s) make(s) it possible to determine information relating to the wearer's motions. For example, a rotational motion toward a persistent horizontal position can be interpreted as the beginning of a resting phase. The module 221 may directly deliver the measurement data and/or make a first processing of such data, for example in order to calculate an energy expenditure value during a given time, such as a game or a phase of play. A speed or acceleration in a vertical direction within a short time can be considered as a jump.

The data acquisition and wireless communication module 222, installed in the first housing 202, is so configured as to retrieve and transmit the motion data and the physiological measurements such as the cardiac rate, the quality of the measurement of the cardiac rate, the respiratory rate, emitted by the sensor module 210 via the wire 231.

Preferably but not restrictively, all such quantities will be updated at intervals of 3 to 6 seconds. In addition, in an advantageous embodiment, the data acquisition module 222 comprises a specific memory element for storing the received motion and/or physiological data. In another embodiment, the data acquisition module 222 sends but does not store the received physiological and/or motion data.

The data acquisition and wireless communication module 222 is installed in the second housing 202 and is so configured as to send the physiological measurements and motion data to the server 260 via the communication system 250. Preferably, but not restrictively, the data acquisition and wireless communication module 222 is a radio module using ISM (industrial, scientific and medical) bands and having a low power consumption, which enables it to operate autonomously for, for example, the whole duration of the game.

The communication between the wireless communication unit 222 and the communication system 250 will be explained in greater details in the following paragraphs.

The power source module 223, installed in the third housing 203, is electrically connected to the other modules respectively to supply these with power: the data acquisition and wireless communication module 222, the motion detection module 221 and the sensor module 210. In a preferred embodiment, the power source module 223 is a rechargeable battery having at least three hours' operation time.

The housings 201, 203 each have a coating made of elastomeric material such as rubber/silicone. The coating of the housing 203 is either made of hard plastic or elastomeric material. Other lightweight, water-resistant and deformable materials are considered as equivalent.

It should be noted that any two modules 201, 202 and 203 may be installed in the same housing without departing from the scope of the present invention.

Figure 4:
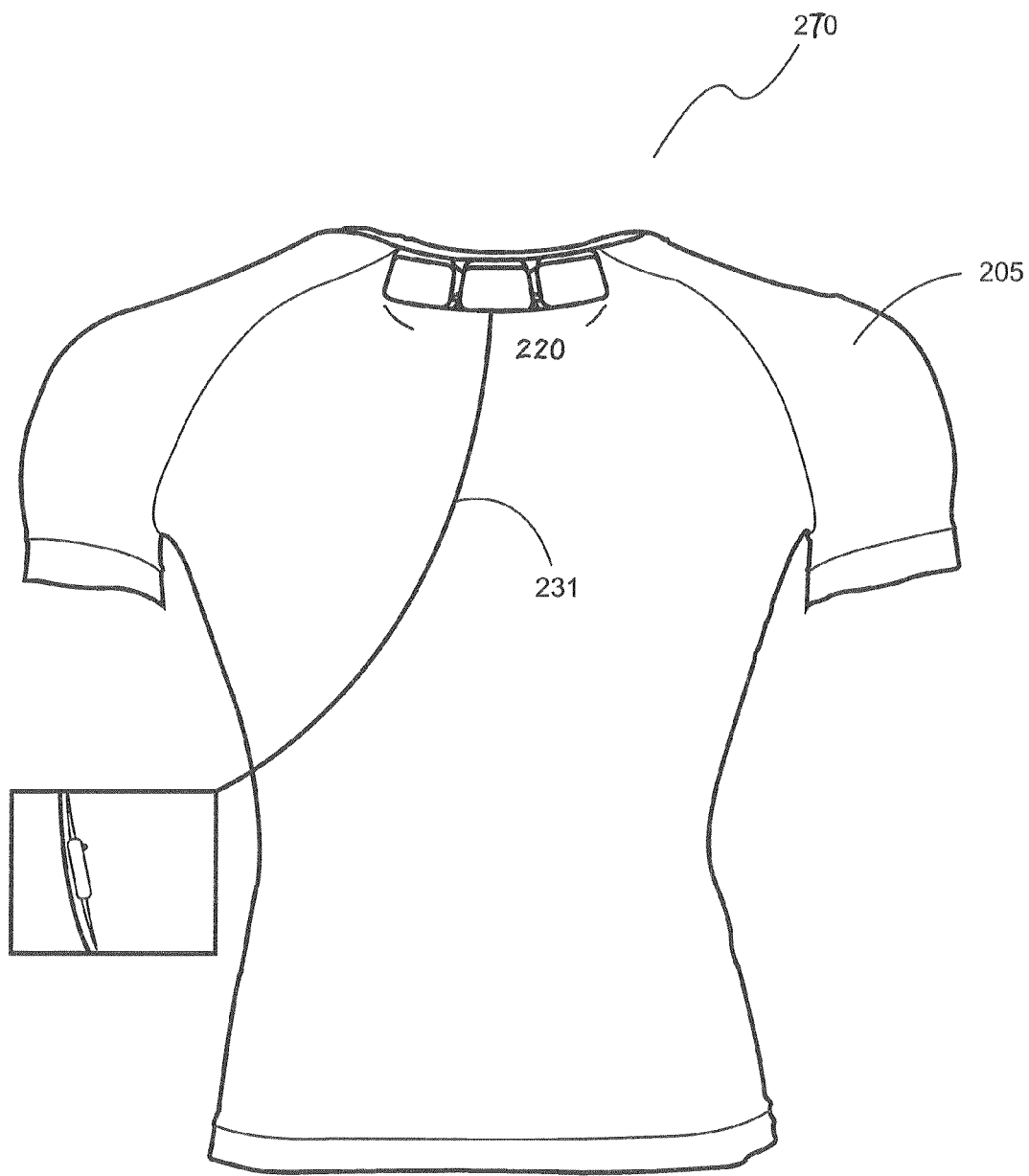
FIG. 4 shows the monitoring system integrated in the back side of the T-shirt at a collar part of the garment according to one embodiment of the present invention.

As illustrated in FIG. 4, the monitoring system 220 is integrated into the back side of the T-Shirt 205. Preferably, but not restrictively, the monitoring system 220 is integrated into the back side of the T-shirt 205 at a collar part of the garment. Collar part means a portion of the garment which is located approximately at the bottom of the nape of the wearer's neck.

For reasons of safety and convenience, the sensor module 210 and the monitoring system 220 should advantageously be optimized as regards size and power consumption. The dimensions and the weight of the sensor module 210 and of the monitoring system 220 must be sufficiently reduced. The monitoring system 220 should also be able to comply with the shape of a part of the body whereon the monitoring system is adapted to be placed.

The dimensions of a housing 201, 202, 203 are preferably but not restrictively 20×20×7 mm, and the weight of the monitoring system 220 is about 17 g.

Furthermore, in order to be able to be placed on the collar part of the T-shirt 205 while complying with the shape of the collar part, the monitoring system 220 preferably comprises two flexible connecting members 211, 212 so configured as to mechanically connect the three boxes 201, 202, 203. More particularly, the first connecting member 211 is installed between the two housings 201, 203 to connect these; the second connecting member 212 is installed between the two housings 202, 203 to connect these. The connecting members 211, 212 are flexible and preferably both deformable in bend in a direction (advantageously a direction perpendicular to the plane of the connecting members 211, 212 and/or the plane wherein the modules are located) and rigid in the other directions, so that the housings 201, 202, 203 can comply with the shape of a part of the body, in particular the one having a curved surface (the wearer's collar, for example) whereon the housings 201, 202, 203 are adapted to be placed.

For this purpose, the connecting members 211, 212 may for example be in the form of straps of a material such as a polymer having a selected thickness, for example less than 0.5 mm, so as to preserve the ability to deform in bend. In another advantageous embodiment, the selected material is an elastomer the flexibility of which provides the capacity of conformation of the assembly.

Several connecting members 211, 212 may be provided between the two housings 201, 202, 203. The connecting members 211, 212 may also have an elongated shape the longitudinal direction of which is oriented along the space between the housings 201, 202, 203, for example as bars or small cross-section cables to allow bending.

The connecting members 211, 212 thus enable the housings 201, 202, 203 to be interconnected in a sufficiently compact manner and not to intersect and create impacts against each other. The wearer's safety, the retrieval of physiological measurements and the remote transmission of data relative to physiological measurements are guaranteed, especially during a training session or a game.

The invention is not limited to the material, to the shape nor to the thickness of the connecting members 211, 212 illustrated in the above example. Other materials, shapes and thicknesses that enable the connecting members 211, 212 to be deformable in bend in one direction and rigid in another direction may be provided without departing from the scope of the present invention.

The connecting members 211, 212 may be added onto the housings 201, 202, 203 whereon they are fixed by any means, or be integral with the housings. In the latter case, a shell portion of the housings 201, 202, 203 and the connecting members 211, 212 connecting these may for example be moulded in one piece.

Moreover, in a preferred but not restrictive embodiment, the connecting members 211, 212 comprise cables (not shown in the Figures) or their equivalents so configured as to electrically connect the three housings 201, 202, 203.

Thus, thanks to the presence of the two connecting members 211, 212, the three boxes 201, 202, 203 are electrically and mechanically flexibly interconnected by the same means to comply with the collar part of the T-Shirt 205.

The snap buttons 235 are installed on the housings 201, 202, 203 and connected to the sensor module 210 via the wired electrical connection system 230. In a preferred embodiment, the snap buttons 235 are used not only as electrical contacts with the sensor module 210, but also for recharging the power source module 223 and participate in the retrieving of physiological measurements. Moreover, the snap buttons 235 are preferably but not restrictively so configured as to secure the housings 201, 202, 203 to the collar part of the T-Shirt 205.

The monitoring system 220 of the invention is not limited to the number of housings and/or to that of the connecting members and/or to the snap buttons mentioned above. Similarly, the modules installed in the housings could be distributed otherwise than the cases described above and illustrated.

Then, as illustrated in FIG. 1, the communication system 250 of the data, more particularly physiological data, collection system 200 comprises a plurality of transmission relays 251a to 251f so configured as to route the physiological measurements and/or motion data, and the server 260 so configured as to receive from the plurality of transmission relays 251 to 251f and store, and sort the physiological measurements by erasing duplicates possibly generated by multiple transmission paths created by the relays.

The plurality of transmission relays 251a to 251f is here installed so as to surround a zone of displacement 252 of the player. In the embodiment, the zone of displacement 252 is the game field. In addition, six transmission relays 251 to 251f are shown in FIG. 1 to facilitate the understanding of the invention. The number of transmission relays is determined by several factors such as the communication range of a communication relay and the surface of the zone of displacement 252, etc. A smaller or greater number of transmission relays can be installed in the communication system 250 without departing from the scope of the present invention.

The installation of the communication relays 251a to 251f aims at providing communication between the (wearer-borne) data acquisition and wireless communication module 222, and the transmission relays 251 to 251, the frequency and power of which are strictly limited to avoid any harmful effects on human health. Preferably but not restrictively, the transmission relays 251 to 251f and the wireless communication module 221 follow a radio communication protocol the frequency of which is below 928 MHz, and the power of which is below 10 dBm. A range of 150 m is satisfactory.

The communication between the transmission relays 251a to 251f and the server 260 can be achieved using various means such as Wifi, cell communication, or a combination of the Wifi connection and/or the wired and/or cell communication, etc. Since the devices 251 to 251f and 260 are not worn by the player, the frequency and the power of such communication are less strictly limited and can thus be higher than those allowed by the radio communication protocol used for the monitoring system 220 for an efficient communication.

In one advantageous embodiment, the communication system 250 comprises an access point 255 used as an intermediate means between the transmission relays 251 to 251f and the server 260. The access point 255 complies, for instance, with two different protocols such as the radio communication one and the Wifi connection one and thus transmits the physiological measurements sent by the transmission relays 251 to 251f to the server 260. The access point 255 is either connected to the server 260 via the Internet connection or installed in a device comprising the server 260.

The communications mentioned in the present description may be wholly or partially encrypted, in particular in the wireless part. All encryption means may be used.

The server 260 may perform several functions, such as receiving the physiological measurements and/or the motion data and storing the physiological measurements and/or the motion data. In addition, it advantageously determines the position of the data collection equipment 270 by a triangulation calculation from three of the six transmission relays 251 to 251f.

Moreover, in one advantageous embodiment, the server 260 is connected to a mobile computer 256 or to other electronic devices (such as a tablet or a smartphone) without, for all that, departing from the scope of the present invention, so as to facilitate the execution of analyses requiring the physiological measurements, and/or viewing of the data, etc.

The invention is not limited to the previously described embodiments, but extends to all the embodiments covered by the claims.

The invention claimed is:

1. A system for collecting physiological data comprising a data collection device comprising at least one sensor module so configured as to capture physiological measurements, and a monitoring system so configured as to retrieve and transmit the physiological measurements, wherein:
    the data collection device comprises a garment wherein the sensor module and the monitoring system are integrated,
    the monitoring system comprises:
    at least two housings connected together mechanically in a flexible manner so as to conform to the shape of a part of the body whereon the monitoring system is able to be positioned;
    at least one flexible connecting member for mechanically connecting the at least two housings;
    a data acquisition and wireless communication module installed in one of the two housings;
    a motion detection module installed in a first housing of the at least two housings, electrically connected to the data acquisition and wireless communication module and so configured as to capture motion data, the data acquisition and wireless communication module being so configured as to retrieve and send the physiological measurements and the motion data to a remote receiver;
    wherein the at least one connecting member is deformable in bend in one single direction of bend and is not deformable in bend in any other directions of bend,
    wherein each of the at least two housings comprises at least one snap button so configured as to fasten said housing to the garment, with at least one snap button being electrically connected to the sensor module via at least one wire of a wired electrical connection system.

2. The system for collecting physiological data according to claim 1, wherein the at least one connecting member extends in a plane and is deformable in bend in one single direction which is perpendicular to the plane.

3. The system for collecting physiological data according to claim 1, wherein the at least one connecting member is in the form of a strap.

4. The system for collecting physiological data according to claim 1, wherein the at least one connecting member is made of a polymeric material.

5. The system for collecting physiological data according to claim 4, wherein the at least one connecting member is so configured as to electrically connect the at least two housings.

6. The system for collecting physiological data according to claim 1, wherein the data acquisition and wireless communication module is installed in a first housing, the motion detection module is installed in a second housing; the monitoring system comprises:
   a power source module installed in a third housing and electrically connected to the data acquisition and wireless communication module and to the motion detection module respectively,
   a first connecting member so configured as to mechanically connect the first and third housings, and
   a second connecting member so configured as to mechanically connect the second and third housings.

7. The system for collecting physiological data according to claim 1, wherein at least one housing comprises a coating made of elastomeric material.

8. The system for collecting physiological data according to claim 1, wherein at least one snap button of the first housing is electrically connected to the data acquisition and wireless communication module.

9. The system for collecting physiological data according to claim 1, wherein the at least one wire of the wired electrical connection system is inserted into a wire passage between the back and the front of the garment.

10. The system for collecting physiological data according to claim 1, wherein the monitoring system is entirely integrated at a collar part of the garment.

11. The system for collecting physiological data according to claim 1, wherein the sensor module comprises at least one textile electrode and/or one textile membrane so configured as to capture the physiological measurements such as cardiac data and a respiration rate.

12. The system for collecting physiological data according to claim 1, wherein the data acquisition and wireless communication module is a radio module.

13. The system for collecting physiological data according to claim 1, which comprises a communication system comprising a plurality of transmission relays so configured as to route the physiological measurements and the motion data, and a server so configured as to receive from the plurality of transmission relays and to store the physiological measurements and the motion data.

14. The system for collecting physiological data according to claim 13, wherein the plurality of transmission relays is installed so as to surround a zone of displacement.

15. The system for collecting physiological data according to claim 13, wherein the position of the monitoring system is detected by triangulation from three of said transmission relays.

16. The system for collecting physiological data according to claim 13, wherein a communication between the plurality of transmission relays and the data acquisition and wireless communication module complies with a radio communication protocol, the frequency of which is below 928 MHz, and the power of which is below 10 dBm.

17. The system for collecting physiological data according to claim 13, wherein the plurality of transmission relays and the server communicate through a communication network comprising at least a portion of wireless communication from the plurality of transmission relays, the frequency and the power of the portion of wireless communication are above those allowed by the radio communication protocol.

18. The system for collecting physiological data according to claim 11, wherein the communication system comprises an access point so configured as to transmit to the server the physiological measurements and the motion data sent from the plurality of transmission relays, with the access point being either connected to the server by an Internet connection or installed in a device comprising the server.

19. A system for collecting physiological data comprising a data collection device comprising at least one sensor module so configured as to capture physiological measurements, and a monitoring system so configured as to retrieve and transmit the physiological measurements, wherein:
   the data collection device comprises a garment wherein the sensor module and the monitoring system are integrated,
   the monitoring system comprises:
   at least two housings connected together mechanically in a flexible manner so as to conform to the shape of a part of the body whereon the monitoring system is able to be positioned;
   at least one flexible connecting member for mechanically connecting the at least two housings;
   a data acquisition and wireless communication module installed in one of the two housings;
   a motion detection module installed in one of two housings, electrically connected to the data acquisition and wireless communication module and so configured as to capture motion data, the data acquisition and wireless communication module being so configured as to retrieve and send the physiological measurements and the motion data to a remote receiver;
   wherein the at least one connecting member is deformable in bend in one single direction of bend and is not deformable in bend in any other directions of bend, and
   wherein the at least one connecting member comprises a body made of a polymer material and wires configured to electrically connect the at least two housings, the body having a larger dimension directed along a longitudinal direction corresponding to a spacing direction between the at least two housings, and
   wherein each of the at least two housings of the monitoring system comprises at least one snap button so configured as to fasten the at least one housing to the garment, at least one snap button being electrically connected to the sensor module via at least one wire of a wired electrical connection system.

* * * * *